(12) United States Patent
Yeh

(10) Patent No.: US 11,701,509 B2
(45) Date of Patent: *Jul. 18, 2023

(54) COMPRESSIBLE CANNULA VALVE

(71) Applicant: CAREFUSION 303, INC., San Diego, CA (US)

(72) Inventor: Jonathan Yeh, Diamond Bar, CA (US)

(73) Assignee: CareFusion 303, Inc., San Diego, CA (US)

( * ) Notice: Subject to any disclaimer, the term of this patent is extended or adjusted under 35 U.S.C. 154(b) by 1084 days.

This patent is subject to a terminal disclaimer.

(21) Appl. No.: 16/427,216

(22) Filed: May 30, 2019

(65) Prior Publication Data

US 2019/0314624 A1    Oct. 17, 2019

Related U.S. Application Data

(63) Continuation of application No. 14/806,469, filed on Jul. 22, 2015, now Pat. No. 10,350,403, which is a continuation of application No. 13/360,180, filed on Jan. 27, 2012, now Pat. No. 9,114,244.

(51) Int. Cl.
*A61M 39/26*  (2006.01)
*A61M 39/24*  (2006.01)

(52) U.S. Cl.
CPC ............ *A61M 39/24* (2013.01); *A61M 39/26* (2013.01); *A61M 2039/2433* (2013.01); *A61M 2039/263* (2013.01); *A61M 2039/267* (2013.01)

(58) Field of Classification Search
CPC ............ A61M 39/26; A61M 2039/2433
See application file for complete search history.

(56) References Cited

U.S. PATENT DOCUMENTS

| | | |
|---|---|---|
| 5,360,413 A | 11/1994 | Leason et al. |
| 5,549,566 A | 8/1996 | Elias et al. |
| 6,050,978 A | 4/2000 | Orr et al. |
| 6,063,062 A | 5/2000 | Paradis |
| 6,168,137 B1 | 1/2001 | Paradis |
| 6,585,229 B2 | 7/2003 | Cote, Sr. et al. |
| 7,118,560 B2 | 10/2006 | Bonaldo |
| 7,753,338 B2 | 7/2010 | Desecki |
| 7,784,766 B2 | 8/2010 | Guala |
| 7,993,328 B2 | 8/2011 | Whitley |

(Continued)

FOREIGN PATENT DOCUMENTS

| | | |
|---|---|---|
| JP | H07505064 | 6/1995 |
| JP | 2007500537 | 1/2007 |

(Continued)

OTHER PUBLICATIONS

European Office Action for Application No. 18159949.9, dated Mar. 2, 2022, 4 pages.

(Continued)

*Primary Examiner* — Jenna Zhang
(74) *Attorney, Agent, or Firm* — Morgan Lewis & Bockius LLP

(57) ABSTRACT

A needleless valve system includes a cannula comprising a cannula tip; a valve comprising a valve tip, wherein the valve is disposed around the cannula; and a housing comprising a housing tip, wherein the cannula tip, the valve tip, and the housing tip comprise a flat surface when the needleless valve system is in a sealed position.

18 Claims, 6 Drawing Sheets

(56) References Cited

U.S. PATENT DOCUMENTS

| | | | |
|---|---|---|---|
| 2002/0032433 A1 | 3/2002 | Lopez | |
| 2005/0038397 A1* | 2/2005 | Newton | A61M 39/045 604/249 |
| 2005/0090805 A1 | 4/2005 | Shaw et al. | |
| 2005/0121638 A1 | 6/2005 | Doyle | |
| 2007/0007478 A1 | 1/2007 | Leinsing et al. | |
| 2008/0103482 A1* | 5/2008 | Fangrow | A61M 39/22 604/523 |
| 2010/0063482 A1 | 3/2010 | Mansour et al. | |
| 2011/0028914 A1 | 2/2011 | Mansour et al. | |
| 2011/0282302 A1* | 11/2011 | Lopez | A61M 39/26 604/246 |

FOREIGN PATENT DOCUMENTS

| | | | |
|---|---|---|---|
| JP | 2008508016 | | 3/2008 |
| JP | 2011500103 | | 1/2011 |
| WO | WO-2005011799 | A1 | 2/2005 |
| WO | WO-2008052140 | | 5/2008 |
| WO | WO-2009125212 | | 10/2009 |
| WO | WO-2010111546 | | 9/2010 |

OTHER PUBLICATIONS

Japanese Office Action for Application No. 2018103946, dated Mar. 19, 2021, 3 pages including machine translation.
Australian Office Action for Application No. 2019204316, dated Jun. 3, 2020, 4 pages.
Japanese Office Action for Application No. 2018-103946, dated Apr. 24, 2020, 3 pages.
Japanese Office Action for Application No. 2018-103946, dated Aug. 20, 2019, 6 pages.
Japanese Office Action for Application No. 2018-103946, dated Oct. 30, 2020, 3 pages including translation.
Australian Examination Report No. 1 for Application No. 2013212342, dated Oct. 20, 2016, 3 pages.
Australian Examination Report No. 1 for Application No. 2017204209, dated Jun. 26, 2018, 8 pages.
Canadian Office Action for Application No. 2862465, dated Jul. 26, 2019, 4 pages.
Canadian Office Action for Application No. 2862465, dated Nov. 13, 2018, 4 pages.
Extended European Search Report for Application No. 13740599.9, dated Jul. 3, 2015, 6 pages.
Extended European Search Report for Application No. 18159949.9, dated May 14, 2018, 7 pages.
International Preliminary Report on Patentability for International Application No. PCT/US2013/022587, dated Jul. 29, 2014.
International Search Report and Written Opinion for International Application No. PCT/US2013/022587, dated May 3, 2013.
Japanese Office Action for Application No. 2014-554780, dated Jan. 30, 2018, 2 pages.
Japanese Office Action for Application No. 2014-554780, dated Jul. 25, 2017, 2 pages excluding translation.
Japanese Office Action for Application No. 2014-554780, dated Nov. 4, 2016, 3 pages excluding English translation.
Japanese Office Action for Application No. 2018-103946, dated May 10, 2019, 5 pages.
Japanese Office Action for Application No. 2021-115625, dated Jun. 3, 2022, 6 pages including translation.

* cited by examiner

COMPRESSIBLE CANNULA VALVE

CROSS-REFERENCE TO RELATED APPLICATIONS

The present application is a continuation of U.S. application Ser. No. 14/806,469, filed Jul. 22, 2015, entitled, "COMPRESSIBLE CANNULA VALVE," which is a continuation of U.S. application Ser. No. 13/360,180, filed Jan. 27, 2012, and issued as U.S. Pat. No. 9,114,244 entitled, "NEEDLELESS VALVE SYSTEM FLUID CONTROL," all of which are hereby incorporated by reference in their entirety for all purposes.

BACKGROUND

Oftentimes, needleless valves include a large interior volume that results in a large amount of residual fluid within the needleless valve after use of the needleless valve. Among other things, the large amount of residual fluid, which was intended to be administered to a patient, is not actually administered to the patient.

Moreover, some needleless valves include a "straight through" fluid flow channel to reduce the amount of residual fluid within the needleless valve. In particular, such devices utilize a split-septum valve to control fluid flow in the "straight through" fluid flow channel. However, a split-septum valve can retain medical fluid, such as blood, which is difficult to remove from within the slit-septum. As a result, the retained blood within the split-septum can lead to the promotion of blood-borne diseases.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1A:
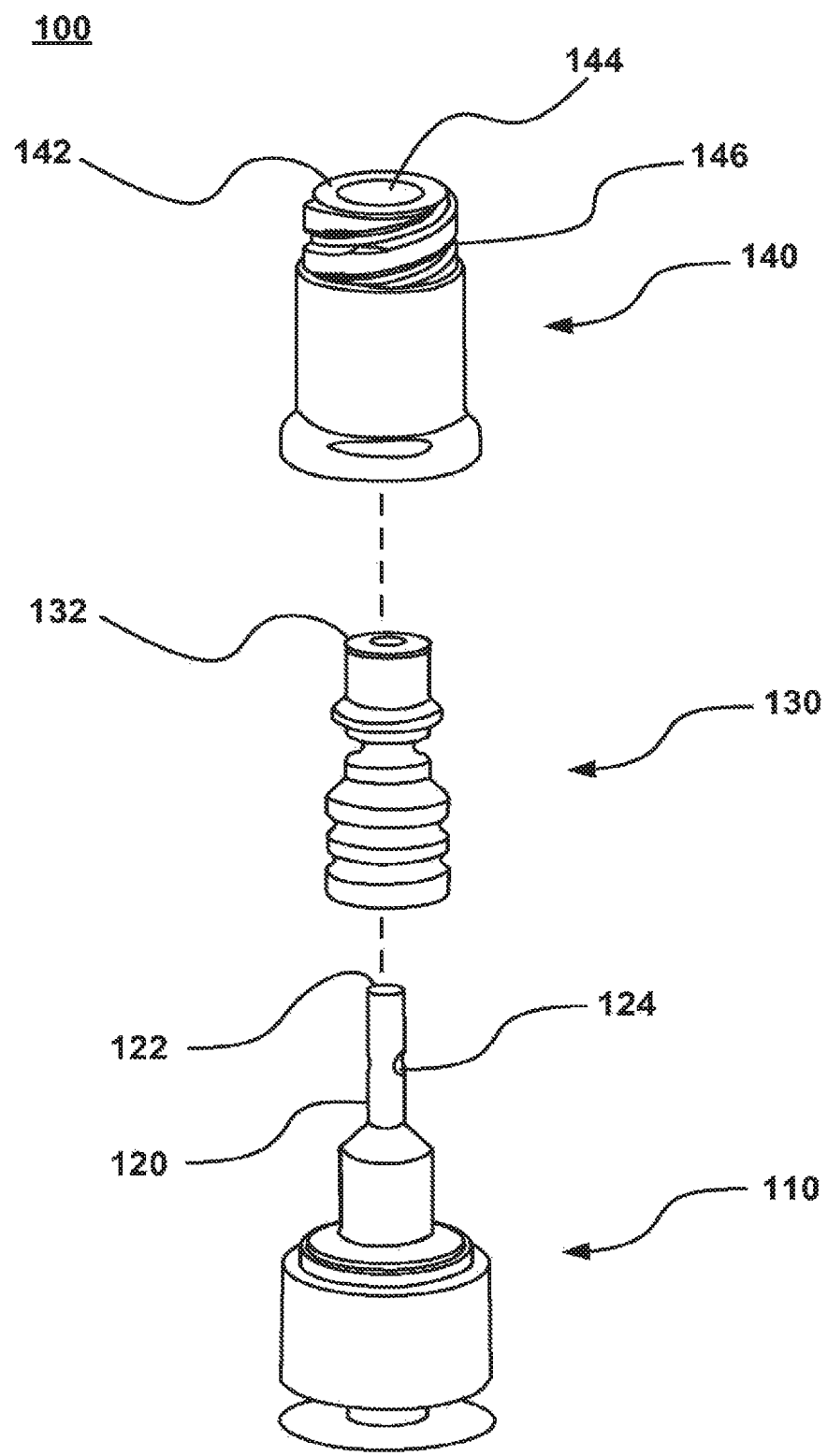
FIGS. 1A-2 depicts embodiments of a needleless valve system.
Figure 1B:
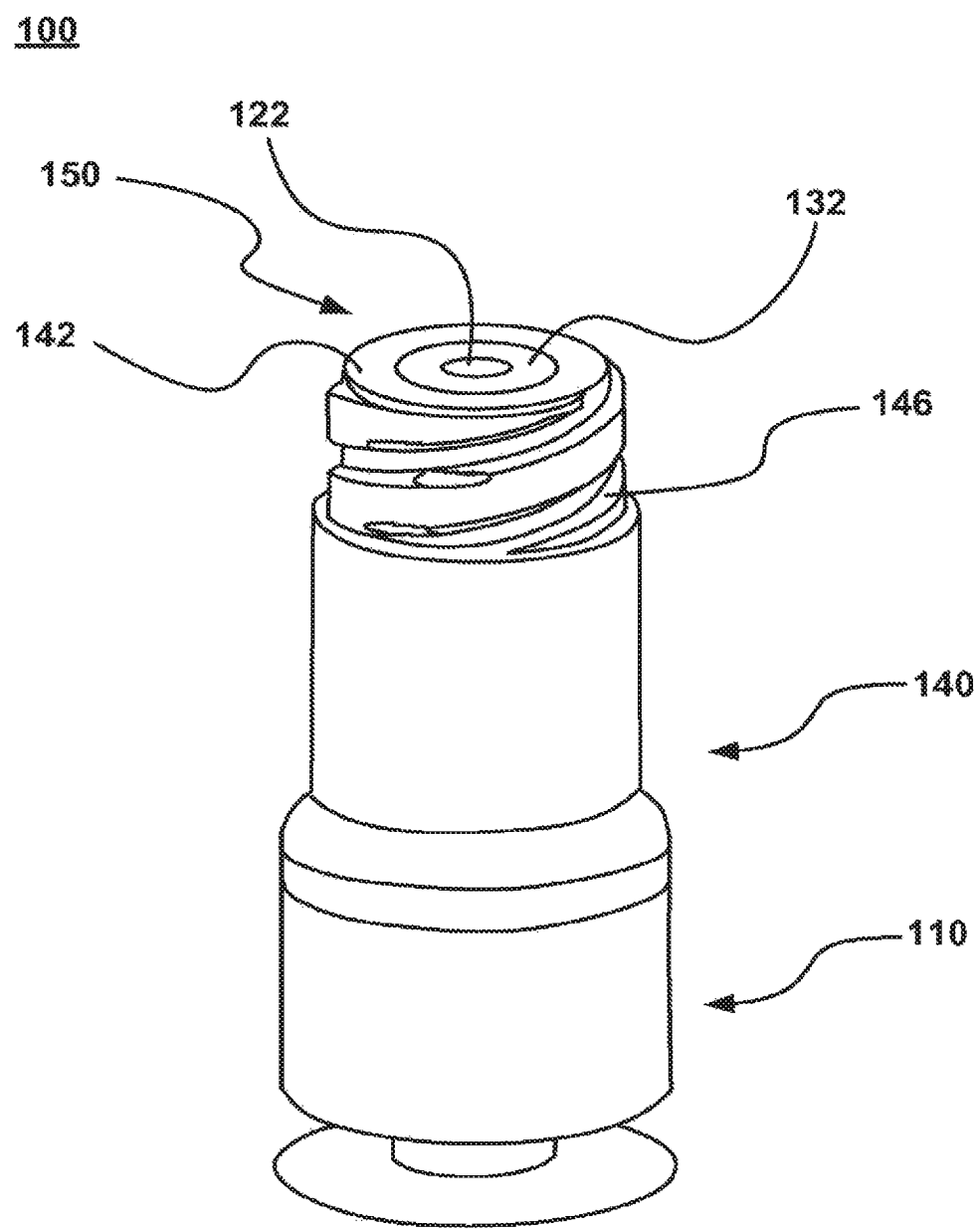
Figure 1C:
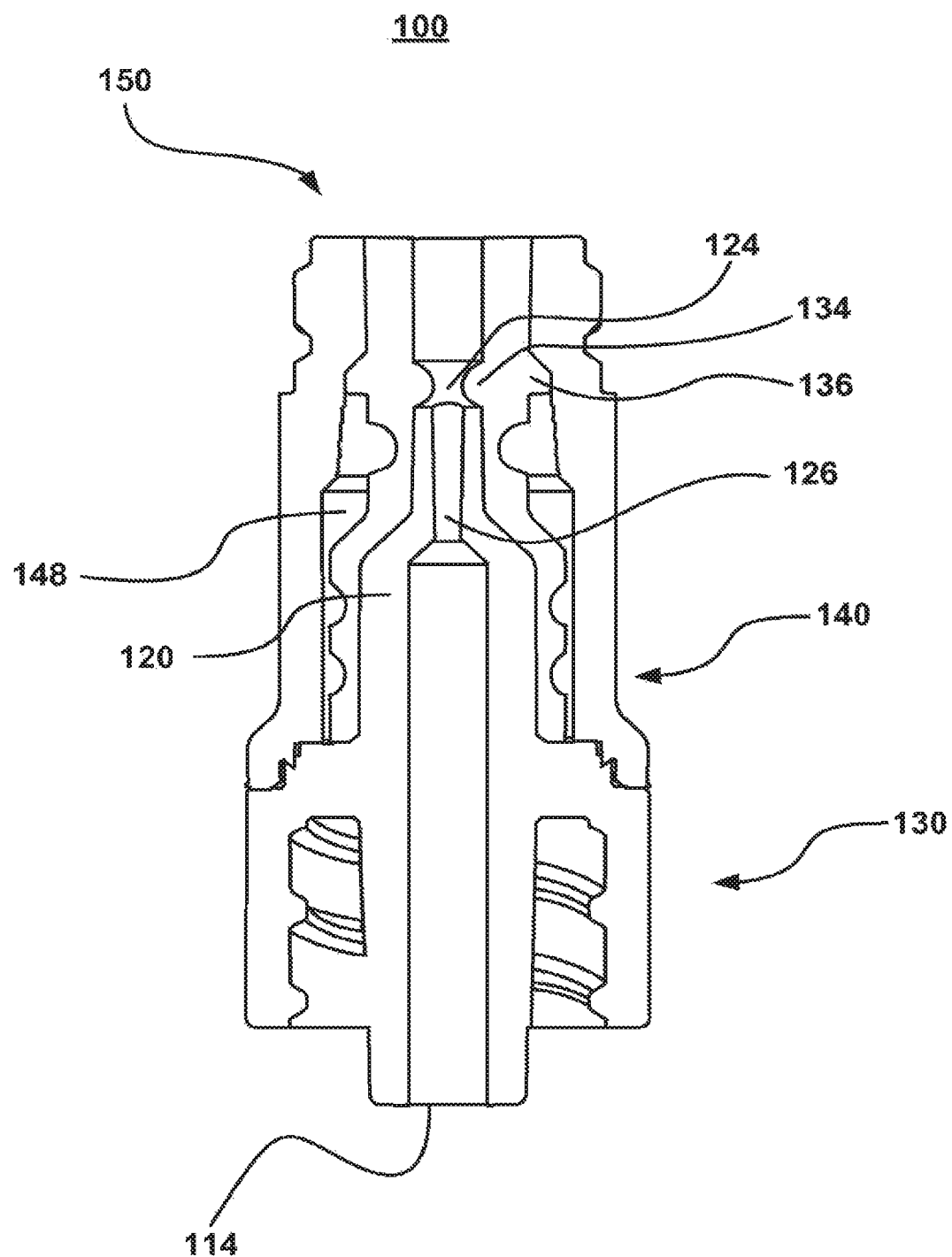
Figure 1D:
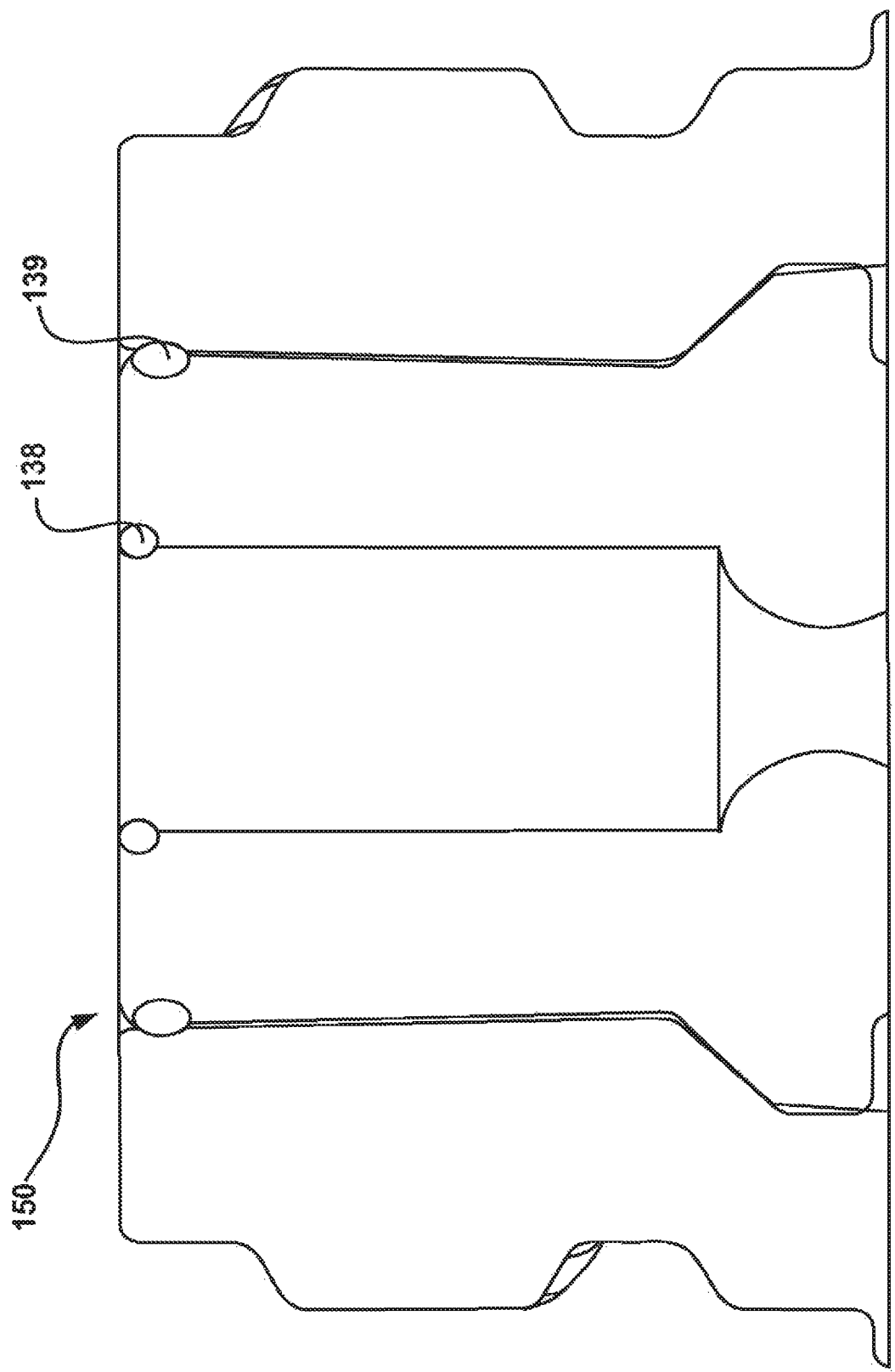

FIGS. 1A-D depicts embodiments of needleless valve system 100 (also referenced herein as system 100) in a sealed or closed position. In particular, FIG. 1A depicts an embodiment of an exploded view of system 100, FIG. 1B depicts an embodiment of a fully assembled system 100, and FIGS. 1C-D depicts embodiments of cross-sectional views of system 100.

System 100 includes base 110 (which includes cannula 120), valve 130 and housing 140. It should be appreciated that base 110 is joined (e.g., ultrasonic welding, adhesive, etc.) with housing 140 such that there is a fluid seal between base 110 and housing 140.

Valve 130 is configured to seal port 124 of cannula 120, which will be described in detail below. Additionally, valve 130 facilitates in sealing port 144 of housing 140. Valve 130 is comprised of a resiliently compressible material that returns to its natural relaxed state when not subject to compression forces.

Cannula 120 is configured to allow for the conveying of fluid in system 100 between port 144 and port 114. In particular, fluid flows through channel 126 when system 100 is in the unsealed or open position.

To seal system 100, valve 130 seals port 124 of cannula 120. Port 124 provides for a fluid channel in the radial direction of cannula 120. In one embodiment, port 124 is a through-hole along a diameter of cannula 120. In another embodiment, port 124 is a hole along a radius of cannula 120.

In one embodiment, valve 130 includes protrusion 134 that seats within port 124. For example, port 124 has two opposing openings and a protrusion seals each of the openings.

In another embodiment, valve 130 includes shoulder 136. Shoulder 136 is disposed opposite protrusion 134. Shoulder 136 seats against an inner surface of housing 140. Shoulder 136 is configured facilitate in the sealing of port 124 by protrusion 134. More specifically, back pressure within fluid channel 126 induces a pressure onto protrusion 134. However, shoulder 136 acts as a buttress and prevents valve 130 (and protrusion 134) from deforming in a radial direction due to the back pressure.

It should be appreciated that port 124 is disposed on a circumference of cannula 120. In contrast, in conventional needleless valve systems, a cannula includes a port on an end portion (e.g., on a longitudinal axis of the cannula).

System 100 includes flat surface 150 when system 100 is in the sealed position. Accordingly, flat surface 150 is able to be properly swabbed. Therefore, pathogens are readily removed and flat surface is properly sanitized.

In particular, tip 122 of cannula 120, tip 132 of valve 130 and tip 142 of housing 140 comprise flat surface 150. As such, system 100 does not require a split septum valve. In contrast, in conventional needleless valve systems, a split-septum valve covers the tip of the cannula and only the split-septum valve and the tip of the housing comprise a top flat surface.

Valve 130 also includes first feature 138 and second feature 139, as depicted in FIG. 1D. First feature 138 and second feature 139 are configured to "squeegee" fluid from the outer surface of cannula 120 and from the inner surface of housing 140, respectively, when valve 130 moves from a compressed position to its relaxed and sealed position, as shown. Accordingly, fluid, such as blood, is expelled from within housing 140.

Figure 2:
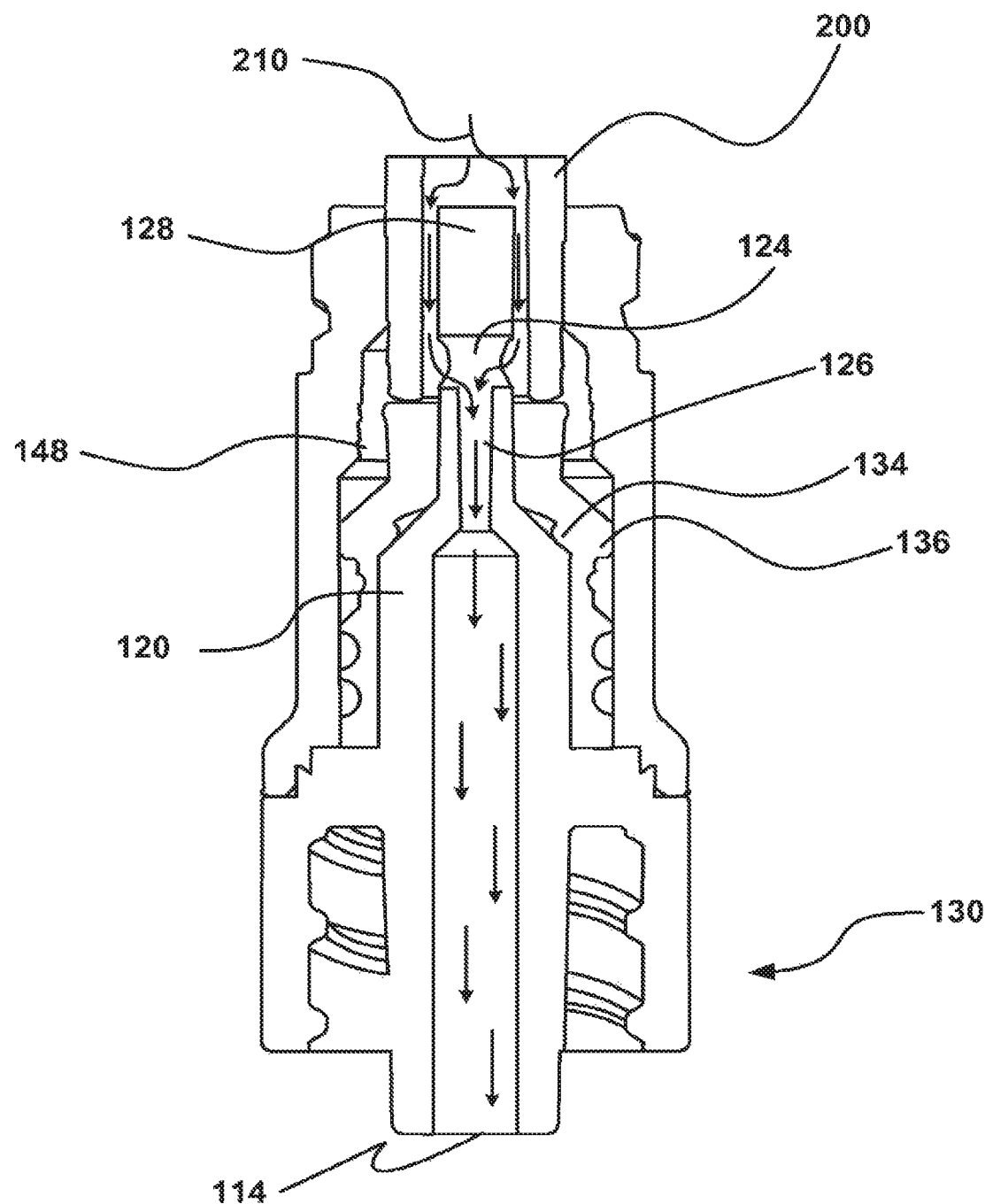

FIG. 2 depicts an embodiment of system 100 in the open or unsealed position. In one embodiment, luer 200 of a needleless device, such as a needleless syringe, enters port 144 and compresses valve 130 within volume 148 of housing 140. In such an embodiment, luer 200 is cooperative with a female luer fitting that threadably engages with male leur fitting 146.

Luer 200 compresses in the longitudinal directions of system 100 and subsequently does not cover port 124. In particular, protrusion 134 resiliently deforms and is forced out of port 124. Accordingly, port 124 is unsealed. Fluid may then travel through system 100 as depicted by fluid flow 210. For example, fluid from an IV bag may flow through system 100 to a patient.

It should be appreciated that fluid flow 210 flows around top portion 128 of cannula 120 and into channel 126 via port 124.

In one embodiment, the fluid can flow in the opposite direction. For example, a clinician may draw blood from a patient and through system 100 into a needleless syringe. For instance, blood flows into system 100 at port 114 and exits system 100 at port 144.

In response to luer 200 being removed from system 100, valve 130 expands to its original position. More specifically, valve 130 expands such that protrusion 134 seats within port 124 and therefore, seals port 124.

As depicted, cannula 120 is coaxial with system 100. As such, fluid flow 210 is through cannula 120. Moreover, the fluid travels exclusively through cannula 120 and does not fill volume 148 or the interior of housing 140. Therefore, there is little residual fluid within system 100.

In contrast, in convention needleless systems, fluid substantially fills the interior volume of the housing which results in a substantial amount of volume. For example, in a convention system, the interior volume may be 1 cubic centimeters (cc). If 10 cc of fluid is intended to be conveyed to a patient via the needleless system, only 9 cc of the fluid reaches the patient, while the other 1 cc remains in the needleless valve as residual fluid.

Figure 3:
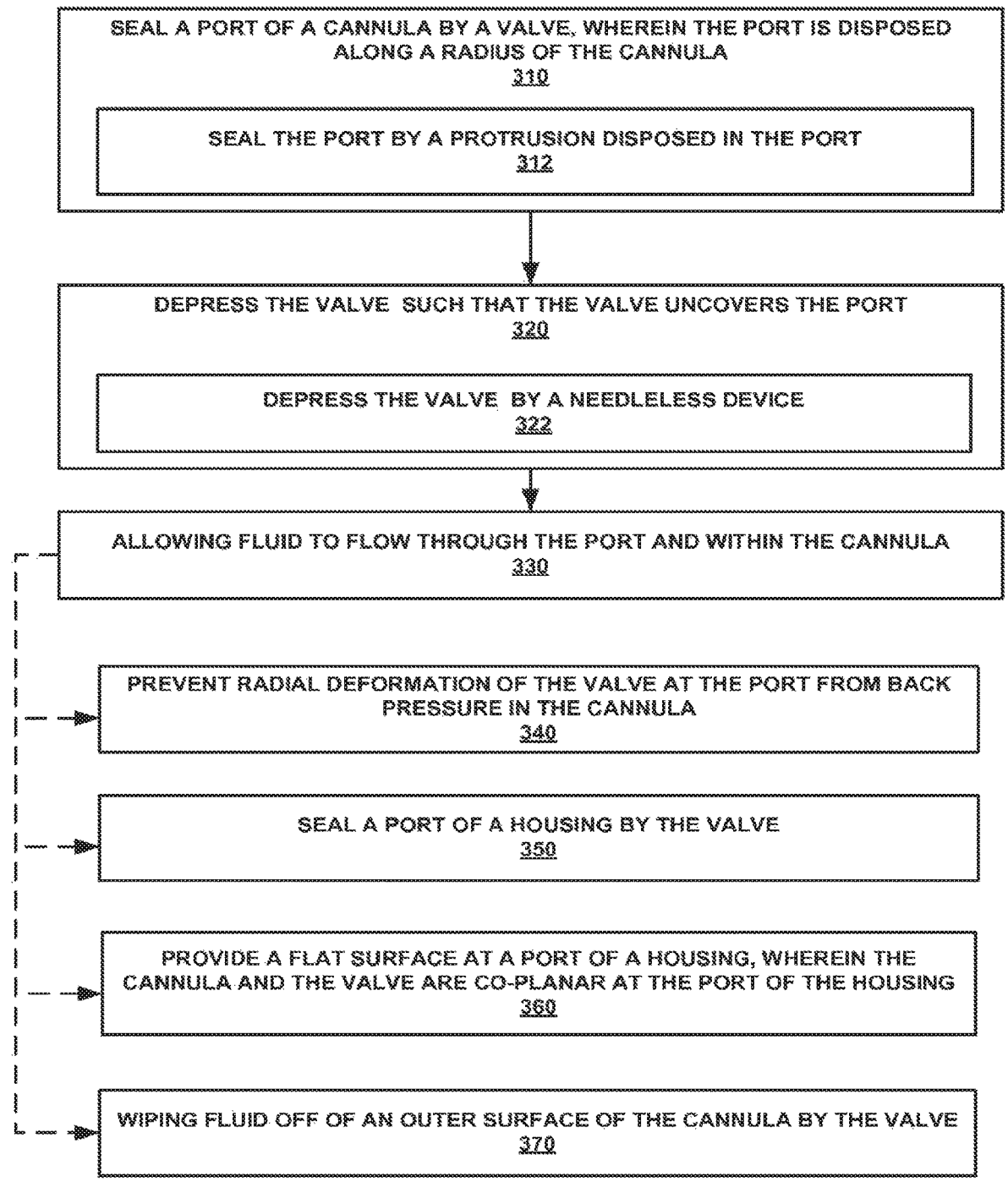
FIG. 3 illustrates an embodiment of a method for controlling fluid flow in a needleless valve system.

FIG. 3 depicts an embodiment of method 300 for controlling fluid flow in a needleless valve system. In various embodiments, method 300 is performed at least by needleless valve system 100, as depicted in FIGS. 1A-2.

At 310 of method 300, a port of a cannula is sealed by a valve, wherein the port is disposed along a radius of the cannula. For example, port 124 is sealed by valve 130. Port 124 is disposed at least along a radius of cannula 120.

In one embodiment, at 312, the port is sealed by a protrusion disposed in the port. For example, port 124 is sealed by protrusion 134 that is at least partially disposed in port 124.

At 320, the valve is depressed such that the valve uncovers the port. For example, valve 130 is depressed (in the longitudinal direction or co-axially with housing 140), such that port 124 is uncovered.

In one embodiment, at 322, the valve is depressed by a needleless device. For example, valve 130 is depressed within housing 140 by luer 200.

At 330, fluid is allowed to flow through the port and within the cannula. For example, in response to port 124 being uncovered, fluid flows through port 124 and in channel 126.

At 340, radial deformation of the valve at the port from back pressure in the cannula is prevented. For example, back pressure within cannula 120 can push against protrusion 134. However, shoulder 136, which seats against the inner surface of housing 140, prevents radial deformation of valve 130 at port 124.

At 350, a port of a housing is sealed by the valve. For instance, valve 130 facilitates in sealing port 144 of housing 140.

At 360, a flat surface is provided at a port of a housing, wherein the cannula and the valve are co-planar at the port of the housing. For example, flat surface 150 is provided at port 144. In particular, tip 122 of cannula and tip 132 of valve 130 are co-planar when system 100 is in the sealed position.

At 370, fluid is wiped off of an outer surface of the cannula by the valve. For example, first feature 138 acts as a squeegee and wipes off an outer surface of cannula 120 when valve 130 moves from a compressed state to a relaxed state. Moreover, second feature 139 also acts as a squeegee and wipes off an inner surface of housing 140 when valve 130 moves from a compressed state to a relaxed state. As a result, fluid that is retained between top portion 128 of cannula 120 and an inner surface of housing 140 is expelled out of port 144 when valve 130 moves from a compressed state to a relaxed state.

Various embodiments of the present invention are thus described. While the present invention has been described in particular embodiments, it should be appreciated that the present invention should not be construed as limited by such embodiments, but rather construed according to the following claims.

What is claimed:

1. A compressible cannula valve comprising:
   a housing comprising an inner cavity and a housing port,
      a cannula positioned in the inner cavity and comprising
      a cannula tip, a central channel, and a radially extending opening in fluid communication with the central channel; and
   a resiliently compressible valve comprising a valve tip, a shoulder, and a protrusion, wherein each of the cannula tip and the valve tip form a flat surface at the housing port, and wherein the valve is disposed in the inner cavity of the housing and around the cannula, and in a sealed position, the protrusion is received radially within the radially extending opening, and the shoulder is disposed opposite the protrusion to engage an inner wall of the housing and resist a backpressure within the central channel against the protrusion;
   wherein when the valve changes from the sealed position to an open position, the valve deforms and withdraws the protrusion of the valve out of the radially extending opening.

2. The compressible cannula valve of claim 1, wherein the cannula and the valve are co-axially disposed in the housing.

3. The compressible cannula valve of claim 1, wherein the valve is configured to be compressed coaxially within the housing by a male luer.

4. The compressible cannula valve of claim 1, wherein the cannula comprises a radially extending second opening.

5. The compressible cannula valve of claim 1, wherein the protrusion is radially extending.

6. The compressible cannula valve of claim 1, wherein in the open position, the cannula tip extends through the valve tip.

7. The compressible cannula valve of claim 1, wherein a circumference of an inner surface of the valve being configured for wiping a fluid off of an outer surface of the cannula.

8. The compressible cannula valve of claim 1, further comprising a base joined with the housing, wherein the cannula is formed in the base.

9. The compressible cannula valve of claim 1, wherein the cannula tip extends toward an opening of the housing.

10. A compressible cannula valve comprising:
    a housing having a housing wall around a cavity and a housing port;
    a cannula having a base, a cannula tip extending within the cavity from the base toward the housing port, and a lumen extending from the base to a radially oriented opening on a side of the cannula below the cannula tip; and a resiliently compressible valve surrounding the cannula and having a valve tip, a shoulder, and a protrusion, the shoulder extending radially toward the housing wall and, when in a sealed position, the protrusion extending radially into the radially oriented opening;

wherein, in the sealed position, the valve tip and the cannula tip are co-planar, and the shoulder and the protrusion are axially aligned with the radially oriented opening.

11. The compressible cannula valve of claim 10, wherein in the sealed position, the cannula tip is surrounded by the valve such that the radially oriented opening is obstructed by the protrusion.

12. The compressible cannula valve of claim 10, wherein in the sealed position, the shoulder engages an inner surface of the housing wall to direct the protrusion into the radially oriented opening.

13. The compressible cannula valve of claim 10, wherein in an open position, the valve is compressed toward the base such that a fluid flow through the radially oriented opening is permitted.

14. The compressible cannula valve of claim 10, wherein in an open position, the cannula tip extends through the valve tip.

15. The compressible cannula valve of claim 10, wherein the cannula comprises a radially oriented second opening.

16. The compressible cannula valve of claim 10, wherein the valve is configured to be compressed within the housing by a male luer.

17. The compressible cannula valve of claim 10, wherein a circumference of an inner surface of the valve being configured for wiping a fluid off of an outer surface of the cannula.

18. The compressible cannula valve of claim 10, wherein a circumference of an outer surface of the valve being configured for wiping a fluid off of an inner surface of the housing wall.

* * * * *